US00PP24984P2

(12) United States Plant Patent
Bergman

(10) Patent No.: US PP24,984 P2
(45) Date of Patent: Oct. 21, 2014

(54) *CHRYSANTHEMUM* PLANT NAMED 'CIDZ0039'

(50) Latin Name: *Chrysanthemum×morifolium*
Varietal Denomination: CIDZ0039

(71) Applicant: Syngenta Crop Protection AG, Basel (CH)

(72) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 80 days.

(21) Appl. No.: 13/694,530

(22) Filed: Dec. 11, 2012

(51) Int. Cl.
*A01H 5/00* (2006.01)

(52) U.S. Cl.
USPC ..... Plt./292

(58) Field of Classification Search
USPC ..... Plt./292
See application file for complete search history.

*Primary Examiner* — Annette Para
(74) *Attorney, Agent, or Firm* — Joshua L. Price

(57) ABSTRACT

A new *Chrysanthemum* plant named 'CIDZ0039' particularly distinguished by the red-purple decorative inflorescences, medium yellow-green foliage color, uniform habit with strong branches and an 8 week black cloth flowering response.

1 Drawing Sheet

Latin name of the genus and species of the plant claimed: *Chrysanthemum×morifolium.*

Varietal denomination: 'CIDZ0039'.

BACKGROUND OF THE NEW PLANT

The present invention comprises a new *Chrysanthemum*, botanically known as *Chrysanthemum×morifolium*, and hereinafter referred to by the variety name 'CIDZ0039'.

'CIDZ0039' is a product of a planned breeding program. The new cultivar has red-purple decorative inflorescences, medium yellow-green foliage color, uniform habit, with strong branches and an 8 week black cloth flowering response.

'CIDZ0039' originated from a hybridization made in February 2007 in a greenhouse in Bogota, Columbia. The female parent was the unpatented, proprietary plant designated 'A7321', with small pink, two-toned inflorescences, with a less vigorous plant habit than 'CIDZ0039'.

The male parent of 'CIDZ0039' was the unpatented, proprietary plant designated as 'A6110' with yellow inflorescences, more disc florets, and a more vigorous habit than 'CIDZ0039'. The resultant seed was sown and grown in a shade structure in July 2007 in Fort Myers, Fla. USA.

'CIDZ0039' was selected as one flowering plant within the progeny of the stated cross in the December 2007 in a shade structure in Fort Myers, Fla.

The first act of asexual reproduction of 'CIDZ0039' was accomplished when vegetative cuttings were propagated from the initial selection in March 2008 in a greenhouse in Fort Myers, Fla.

BRIEF SUMMARY OF INVENTION

Horticultural examination of plants grown from cuttings of the plant initiated in March 2008, and continuing thereafter, has demonstrated that the combination of characteristics as herein disclosed for 'CIDZ0039' are firmly fixed and are retained through successive generations of asexual reproduction.

'CIDZ0039' has not been observed under all possible environmental conditions. The phenotype may vary significantly with variations in environment such as temperature, light intensity, and day length.

Plant Breeder's Rights for this cultivar were applied for at the Community Plant Variety Office on Oct. 18, 2011 (11-2484), in Canada on Jun. 29, 2012 (12-7646), and in Brazil on Aug. 14, 2012 (21806.000185/2012). 'CIDZ0039' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIDZ0039' with colors being as true as possible with an illustration of this type. The photographic drawing shows a flowering plant of the new variety, and a close-up of the inflorescence.

DETAILED BOTANICAL DESCRIPTION

The plant descriptions, measurements, and aforementioned photographs were taken in Gilroy, Calif. in early October 2012 under natural light. These plants were grown 4 plants in a 6-inch container in a greenhouse in Nipomo, Calif. These plants used in the photograph and descriptions were about 10-12 weeks old.

Color references are made to The Royal Horticultural Society Colour Chart (R.H.S.) 2001.

TABLE 1

DIFFERENCES BETWEEN THE NEW VARIETY 'CIDZ0039' AND A MOST SIMILAR VARIETY

| | 'CIDZ0039' | 'Dark Pomona' (U.S. Plant Pat. No. 7,842, expired) |
|---|---|---|
| Ray floret color: | Somewhat darker, more reddish tones | Somewhat lighter, more purplish tones |
| Plant habit: | Shorter, more compact | Taller, less compact |
| Flowering response: | 1 week faster | 1 week slower |

Plant:

*Form, growth and habit*.—Herbaceous pot-type, stems upright, uniform and strong growth habit.

*Plant height*.—22-25.0 cm.

*Plant height* (*inflorescence included*).—24-30.0 cm.

*Plant width*.—About 25.0 cm.

Roots:

*Number of days to initiate roots*.—About 4 days at about 22 degrees C.

*Number of days to produce a rooted cutting*.—4-6 days at 22 degrees C.

*Type*.—Fine, fibrous, free branching.

*Color*.—RHS N155B but whiter.

Foliage:

*Arrangement*.—Alternate.

*Immature, leaf color, upper surface*.—Closest to RHS 147A.

*Immature, leaf color, lower surface*.—Closest to RHS 137B.

*Mature, leaf color, upper surface*.—Lighter than RHS 147A.

*Mature, leaf color, lower surface*.—Between RHS 137B and RHS 137C.

*Length*.—8-8.5 cm.

*Width*.—5.3-6.4 cm.

*Shape*.—Ovate.

*Base shape*.—Attenuate.

*Apex shape*.—Mucronulate.

*Margin*.—Slightly palmately lobed; dentate.

*Texture, upper surface*.—Bifid T-shaped hairs.

*Texture, lower surface*.—Bifid T-shaped hairs.

*Color of veins, upper surface*.—RHS 144B.

*Color of veins, lower surface*.—RHS 144B.

*Pattern of veining*.—Palmate.

*Petiole color*.—RHS 144B.

*Length*.—1.8-2.0 cm.

*Diameter*.—0.3 cm.

*Texture*.—Bifid T-shaped hairs.

Stem:

*Quantity of main branches per plant*.—5-7.

*Color of stem*.—RHS 138A but appears lighter due to the hairs.

*Length of stem*.—18-20.0 cm.

*Diameter*.—0.4-0.5 cm.

*Length of internodes*.—0.5-0.9 cm.

*Texture*.—Bifid T-shaped hairs.

*Color of peduncle*.—RHS 138A but appears lighter due to the hairs.

*Length of peduncle*.—4.3-5.5 cm.

*Peduncle diameter*.—0.2 cm.

*Texture*.—Bifid T-shaped hairs.

Inflorescence:

*Type*.—Compositae, solitary decorative inflorescence, borne terminally above foliage, ray florets arranged acropetally on a capitulum.

*Quantity of short days to flowering* (*response time*).—About 56-60 days.

*Natural season flowering*.—Has not been determined on this variety.

*Quantity of inflorescences per plant*.—4-9 with approximately 12-23 buds in various stages.

*Lastingness of individual blooms on the plant*.—About 4 weeks.

*Fragrance*.—Slightly spicy.

Bud (just when opening/showing color):

*Color*.—Shades of and between RHS 182A and RHS 182B.

*Length*.—1-1.5 cm.

*Width*.—1.3-1.5 cm.

*Shape*.—Oblate.

Immature inflorescence:

*Diameter*.—5.5-6.0 cm.

*Color of ray florets, upper surface*.—Between RHS 186A and RHS 186B, overlaid with between RHS 60B and RHS 60C in a slight cross-hatched pattern.

*Color of ray florets, lower surface*.—Lighter than RHS 51D with a deeper hue down the middle of petal.

Mature inflorescence:

*Diameter*.—7.5-8.0 cm.

*Depth*.—2.0 cm.

*Total diameter of disc*.—Is not seen at this stage.

*Receptacle color*.—RHS 145B.

*Receptacle height*.—0.5 cm.

*Receptacle diameter*.—0.6 cm.

Ray florets:

*Average quantity of florets*.—About 160 in numerous whorls (consisting of about 5-60 mature florets and the rest immature florets).

*Color of florets, upper surface*.—Between RHS 186B and RHS 186C, overlaid with RHS 60C in a slight cross-hatched pattern.

*Color of florets, lower surface*.—Closest to RHS 186D but lighter and greyer, overlaid with hues of RHS 186C in a cross-hatched pattern and running a deeper hue down the keels of the petals.

*Length*.—3.5-3.6 cm.

*Width*.—1.0-1.3 cm.

*Shape*.—Broadly elliptical to slightly obovate.

*Apex shape*.—Irregularly emarginate.

*Base shape*.—Cuneate.

*Margin*.—Entire.

*Texture, upper surface*.—Papillose.

*Texture, lower surface*.—Papillose.

Disc florets:

*Average quantity of florets*.—20-25.

*Color of florets*.—RHS 155C base with RHS 13A apex.

*Length*.—0.4 cm.

*Width*.—0.1 cm.

*Shape*.—Tubular, elongated.

*Apex shape*.—Acute, 5 pointed.

*Texture, inner surface*.—Glabrous.

*Texture, outer surface*.—Glabrous.

Phyllaries:

*Quantity*.—About 40-60, consisting of about 10-20 outer and the rest within.

*Color, upper surface*.—The outer ones are about RHS 137B, and the inner ones are RHS 138B.
*Color, lower surface*.—The outer ones are about RHS 137B, and the inner ones are RHS 138B.
*Length*.—0.7-0.8 cm.
*Width*.—0.1-0.2 cm.
*Shape*.—Lanceolate.
*Apex shape*.—Acute.
*Base*.—Fused.
*Margins*.—Entire; the inners ones are papery and translucent.
*Texture, upper surface*.—Glabrous.
*Texture, lower surface*.—Bifid T-shaped hairs.

Reproductive organs:

*Pistil*.—1, found on both types of florets.
*Length*.—0.6-0.7 cm.
*Style color*.—RHS 1C.
*Style length*.—0.6 cm.
*Stigma color*.—RHS 9C.
*Stigma shape*.—Bi-parted.
*Ovary color*.—RHS 155C.
*Ovary length*.—0.1 cm.
*Ovary width*.—0.1 cm.
*Stamens*.—4, found on only on the disc florets.
*Color of filaments*.—RHS 1C.
*Length filaments*.—0.15 cm.
*Anther color*.—RHS 15D.
*Anther length*.—0.15 cm.
*Anther shape*.—Oblong.
*Color of pollen*.—RHS 15B.
*Pollen amount*.—Normal.
*Fertility/seed set*.—Has not been observed to date.
*Disease/pest resistance*.—Has not been observed to date.

What is claimed is:

1. A new and distinct variety of *Chrysanthemum* plant named 'CIDZ0039' substantially as illustrated and described herein.

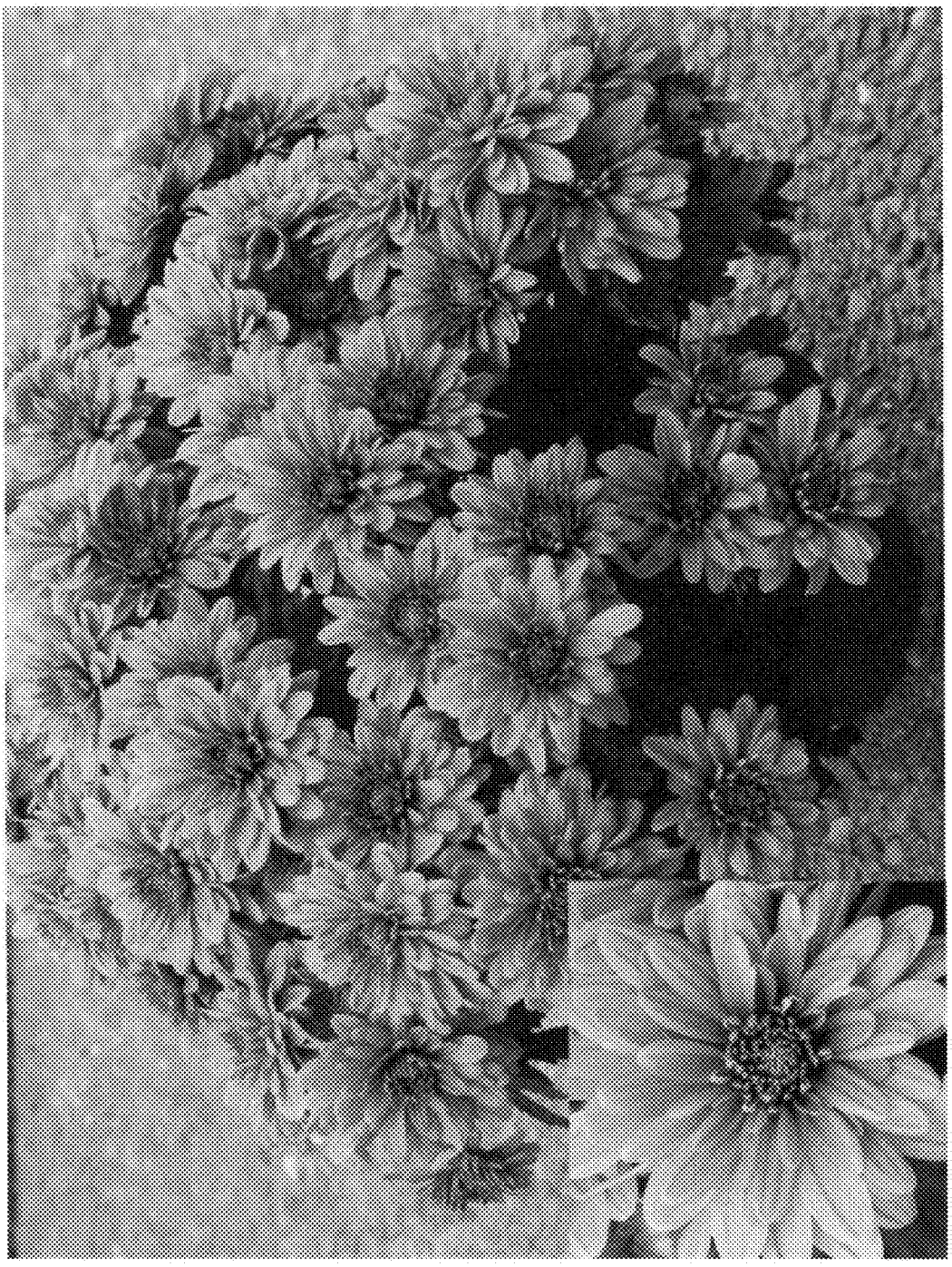

* * * * *